United States Patent [19]

Lin et al.

[11] Patent Number: 4,935,361
[45] Date of Patent: Jun. 19, 1990

[54] CLONING AND EXPRESSION OF T4 DNA POLYMERASE

[75] Inventors: Tsung-Chung Lin, North Haven; William Konigsberg, New Haven; Eleanor Spicer, Milford; John E. Rush, New Haven, all of Conn.

[73] Assignee: Yale University, New Haven, Conn.

[21] Appl. No.: 909,060

[22] Filed: Sep. 18, 1986

[51] Int. Cl.$^5$ .................. C12N 15/00; C12N 1/20
[52] U.S. Cl. .................. 435/172.3; 435/193; 435/194; 435/320; 435/252.3; 435/252.33; 536/27; 935/29; 935/41; 935/56; 935/73
[58] Field of Search .......... 435/194, 172.3, 320, 435/68, 70, 253, 255, 849, 317.1, 252.3, 252.33; 935/29, 41, 56, 73

[56] References Cited

U.S. PATENT DOCUMENTS 4,767,708  8/1988  Minkley et al. .................. 435/194

OTHER PUBLICATIONS

Miller, R. C. et al., Regulation of the Synthesis of the T4 DNA Polymerase (Gene 43); Virology 110, pp. 98–112 (1981).

Holland, M. J. et al., Isolation and Characterization of a Generic Coding for G-3P-Dehydrogenase from *S. cerevie;* J. Biol. chem. 254 (12), pp. 5466–5479 (1979).

Morris, C. F. et al., J. Biol. Chem. 254, 6787–6796 (1979), p. 2, lines 24–28.

Wilson, G. G. et al., Mol. Gen. Genet. 156, 203–214 (1977): p. 2, line 28 to p. 3, line 1.

*Primary Examiner*—Robin L. Teskin
*Attorney, Agent, or Firm*—Millen, White & Zelano

[57] ABSTRACT

The DNA sequence encoding T4 DNA polymerase (gene 43 of T4 phase) has been successfully cloned, thereby providing a convenient source of this enzyme. The method involves the production of a gene 43 NH$_2$-terminus fragment absent its promoter. The latter is ligated to a fragment containing the remaining COOH-terminus sequence but lacking base pairs beyond this terminus which heretofore caused destabilization effects in cloning. The full sequence of the DNA sequence has been elucidated. Corresponding cloning methods are disclosed.

22 Claims, 8 Drawing Sheets

CLONING AND EXPRESSION OF T4 DNA POLYMERASE

BACKGROUND OF THE INVENTION

Bacteriophage T4 codes for all the essential proteins involved in its DNA replication. At present, eleven gene products are implicated in the replication process. The functions of eight of these have been clearly identified (for a review see Nossal, N. G. and Alberts, B. M. (1983) in "Bacteriophage T4", eds. Mathews, C. K., Kutler, E. M., Mosig, G. and Berget, P. B. (*Am. Soc. Microbiol.*, Washington, D.C.), pp. 71-81). They are products of gene 43 (DNA polymerase), gene 32 (helix destabilizing protein), genes 44 and 62 (a complex with DNA-dependent ATPase activity), gene 45 (stimulates 44/62 protein complex ATPase), gene 41 (helicase), gene 61 (RNA priming protein), and gene dda (delicase). DNA polymerase is absolutely required for the initiation and maintenance of viral replication. DNA polymerase was first identified as the product of gene 43 when mutants of the latter were shown to lack a functional polymerase (Warner, H. R. and Barnes, J. E. P (1966). *Virology* 28: 100-101).

The purified T4 polymerase is a monomer of about 110 kilodaltons. It catalyzes three reactions: (i) 5' to 3' polymerization on a primed single-stranded DNA template; (ii) 3' to 5' exonucleolytic hydrolysis of single-stranded DNA and of the 3'—OH end on duplex DNA at a slower rate; and (iii) primer-template dependent turnover of dNTP to dNMP (Goulian, M. Lucas, Z. J., and Kornberg, A. (1968), *J. Biol Chem*, 243:627-638; and Hershfield, M. S. and Nossal, N. G. (1972), *J. Biol Chem.*, 247: 3393-3404). The turnover activity appears to be a result of hydrolysis of newly incorporated nucleotides of the 3' terminus.

Gene 43 is transcribed from its own promoter into a monocistronic mRNA (Young, E. T. and Menard, R. C. (1981), *J. Virol.* 40: 772-789). The level of gene 43 production is self-regulated. T4 phage carrying mutations of gene 43 greatly overproduce a defective polymerase (Russel, M. (1973), *J. Mol. Biol.*, 79: 83-94). This regulation occurs at the level of transcription (Krisch, N. H., van Houwe, G., Belin, D., Gibbs, W. Epstein, R. H. (1977), *Virology*, 78: 87-98). The amount of polymerase produced is also increased by mutations in genes 44 and 45, leading to the suggestion that autoregulation of gene 43 expression is enhanced when the polymerase is associated in a complex with at least gene products of 44 and 45 (Miller, R. C., Young, E. T., Epstein, R. H., Krisch, H. M., Mattson, T. and Bolle, T. A. (1981), *Virology*, 110:98-112).

T4 DNA polymerase is an ideal system for studies of the structure and function of a DNA polymerase. It also is an important enzyme for molecular biologists in the process of DNA manipulation. (See, e.g., Maniatis, infra.) Unfortunately, purification of T4 DNA polymerase from T4 infected *E. coli* cells is time consuming and provides only small amounts of pure protein (Morris, C. F., Hama-Inaba, H., Mace, D. Sinha, N. K., and Alberts, B. M. (1979), *J. Biol. Chem.*, 254:6787-6796). Attempts to clone the entire gene 43 have not been successful. However, a large DNA fragment containing the NH-terminal of gene 43 has been cloned (Wilson, G. G., Tanyashin, V. I., and Murray, N. E., (1977), *Molec. Gen., Genet.*, 156: 203-214). As determined by results of experiments reported in this application, this fragment contained approximately 99% of the gene. Nevertheless, heretofore, it has not been possible to obtain gene 43 in a clonable form.

This is due in part to the fact that straightforward expression of a complete version of gene 43 is inapplicable since T4 DNA polymerase is toxic to bacteria such as *E. coli* the most likely host. Moreover, using conventional restriction endonuclease procedures, it has not been possible to excise a DNA sequence containing complete gene 43 in a fashion in which it is clonable. Consequently, a need has remained to provide a method enabling the cloning of the DNA sequence encoding T4 DNA polymerase.

SUMMARY OF THE INVENTION

Accordingly, it is an object of this invention to provide a method enabling the cloning of the T4 DNA polymerase gene and to provide the resultant T4 DNA polymerase in large and economical quantities.

Upon further study of the specification and appended claims, further objects and advantages of this invention will become apparent to those skilled in the art.

These objects have been achieved by employing an entirely new strategy. In two major aspects, this invention has been accomplished by removing the natural promoter from the $NH_2$-terminus of gene 43 (without removing the ribosome binding site) and by providing techniques for obtaining the intact gene having a COOH-terminus region containing extra sequences, if any, which are ineffective to destabilize vectors into which the gene may be placed for expression.

It has been discovered that the COOH-terminus is followed by a DNA sequence which strongly destabilizes plasmid vectors into which it is inserted. Without wishing to be bound by theory, it is believed this region encodes a very strong promoter. Consequently, it has been discovered that it is critical to ensure that any extension of the COOH-terminus, contains a number of base pairs insufficient to constitute the destabilizing region. Moreover, if the DNA sequence including gene 43 is not devoid of its natural promoter when used to transform a host, its promoter will regulate the gene to express toxic T4 DNA polymerase under cell growth conditions thereby killing the host.

Accordingly, in one aspect, this invention relates to a recombinant cloning vector comprising a DNA sequence encoding a polypeptide having bacterial phage T4 DNA polymerase activity, excluding DNA sequence regions which interfere with the cloning process.

In another aspect, this invention relates to the DNA sequence itself and to a microorganism or cell culture transformed with a corresponding vector containing the sequence.

In a further aspect, this invention relates to a method for producing T4 DNA polymerase comprising expressing the DNA sequence of this invention in a recombinant host. Preferably the sequence is inserted into a plasmid having an inducible promoter for controlling the sequence. Preferably, this inducible promoter is temperature controlled or repressor/inducer controlled. Preferred promoters are λ phage PL promoter in combination with temperature sensitive repressor gene CI857 or is IPTG inducible ptac promoter in cases where the host itself encodes for the lac repressor.

In yet another aspect, this invention relates to a method for producing T4 DNA polymerase comprising transforming a host cell culture with a plasmid of this invention to obtain a recombinant host cell, culturing the recombinant host cell under conditions permitting expression of the T4 DNA polymerase-encoding sequence of the plasmid to produce T4 DNA polymerase and recovering the T4 DNA polymerase.

In a further aspect, this invention relates to a method of obtaining a clonable DNA sequence encoding T4 DNA polymerase, comprising providing a DNA fragment encoding a region from the $NH_2$ terminus of said T4 DNA polymerase, excluding its natural promoter, to a site before its COOH terminus, and ligating to said site a DNA fragment encoding a region of the T4 DNA polymerase from said site to its COOH terminus and excluding natural sequences beyond the COOH terminus which will destabilize a vector to be used to clone said DNA sequence. Typically, the site is a restriction site, preferably the Hind III site adjacent to the gene COOH-terminus.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views, and wherein.

DETAILED DISCUSSION

Figures 1B, 1C:
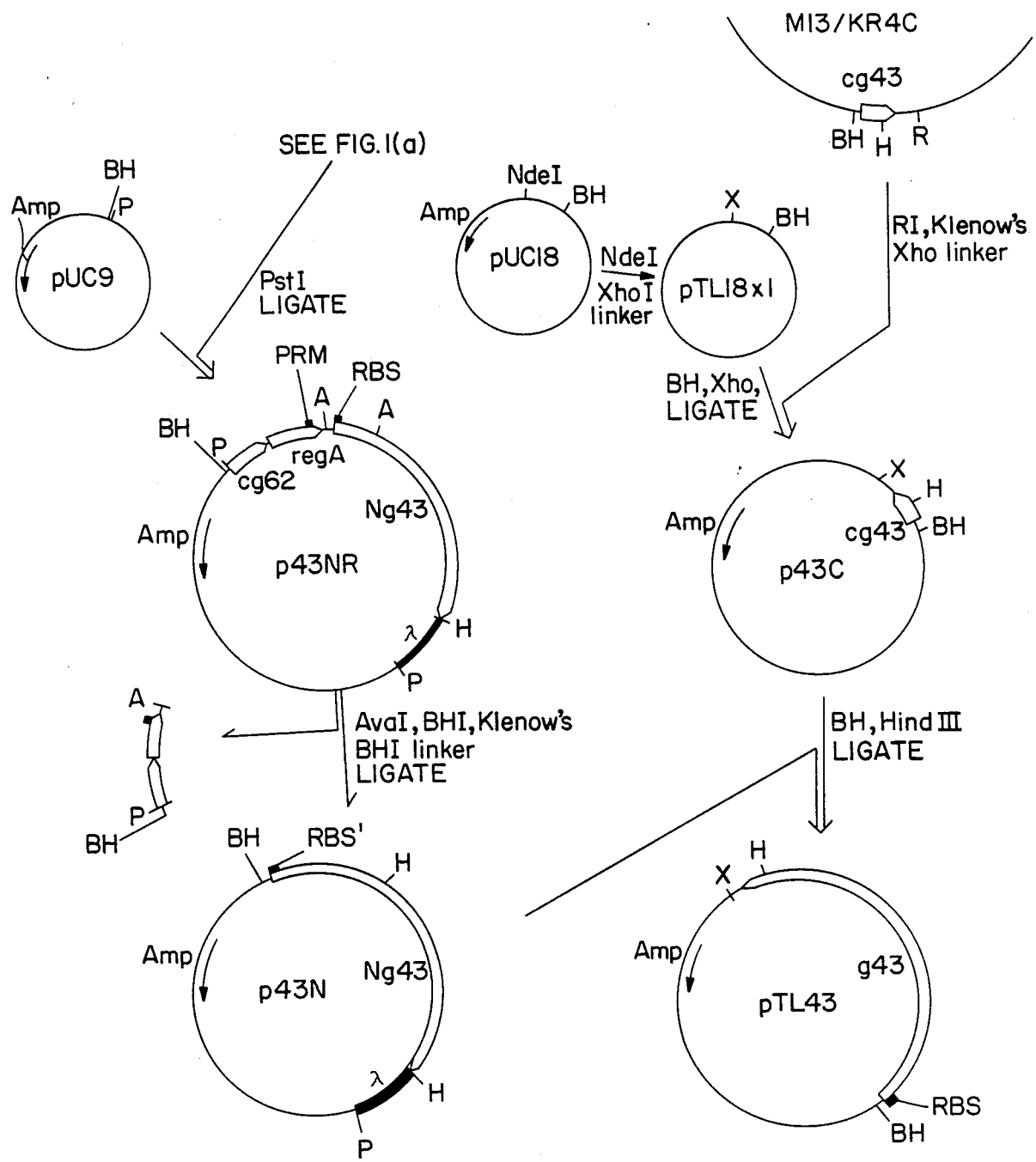
FIGS. 1b and 1c illustrate recombinant processes used to incorporate intact gene 43 into a plasmid.

Throughout the following, the conditions for restriction digestion, DNA ligation, blunt-ending using the Klenow's fragment etc. are those suggested by the manufacturers of the reagents used. Agarose gel electrophoresis, purification of plasmids, and all other techniques used in the various recombinant procedures described below, unless indicated otherwise, are all fully conventional as thoroughly discussed in the literature, e.g., in Maniatis, T., Fritsch, E. F. and Sambrook, J. (1982) *Molecular Cloning: A Laboratory Manual* (Cold Spring Harbor Laboratory, Cold Spring Harbor, N.Y.), which is entirely incorporated by reference herein. Similarly, in accordance with the guidance provided by this application, this invention can be carried out using materials which are readily available or readily preparable in accordance with methods discussed in the literature. For the experiments described herein, the *E. coli* K-12 derivative 71-18 (Δ(lac, pro), sup E, thi, F'proAb, lacIq,ΔZ M15) was obtained from B. Bachman (Genetic Strain Center, Yale University). Many other strains can be fully equivalently used, e.g., JM101, JM103, JM105, JM107, JM109 (all available from BRL), RB-3, etc. All have strong lac genes making them employable also with pTL43Q as discussed below. Plasmids pUC9, pUC18 and bacteriophage mp8 and mp18 were from Bethesda Research Laboratories. Plasmid pGW7, phage λ 761-4 and cytosine-containing T4 phage alcGT7 (Kutter, E. and Snyder, L. (1983) in "Bacteriophage T4", eds. Mathews, C. K., Kutter, E. M., Mosig, G. and Berget, P. B. (Am. Soc. Microbiol, Washington, D.C.), pp. 56–57) were obtained from G. G. Wilson (New England Biolabs). Plasmid ptac12 was provided by J. Brosius (Amann, E., Brosius, J. and Ptashne, M., *Gene*, 25: 167-178).

Restriction endonucleases were purchased from New England Biolabs or Boehringer Mannheim. T4 polynucleotide kinase and BH1 linker (CCGGATCCGG) were purchased from Bethesda Research Laboratories, xhoI linker (CCTTGAGG) was from Pharmacia, and SalI linker (GGTCGACC) was from New England Biolabs.

Many alternative bacteria, bacteriophages, plasmids, vectors, enzymes, linkers, etc. can be employed instead of these in order to carry out varying embodiments of this invention with appropriate strategy modifications made evident by the details of this disclosure. For example, other good candidate plasmids include but are not limited to ptac 11, ptac 12H, pKK233-2, pGW8, PLλ(Pharmacia).

A first step of this invention is to obtain a gene 43 fragment including base pairs from its $NH_2$-terminus to a site before the COOH-terminus. The gene's promoter, as explained above, must be removed from the $NH_2$ terminus but not the ribosome binding site.

The phage T4 DNA polymerase (gene 43) maps next to its own accessory proteins (genes 45, 44 and 62) and regA gene which regulates the translation of the accessory proteins. The DNA sequences of genes 45, 44, 62, regA, and the $NH_2$-terminus of gene 43 have been reported (Spicer, E. K. and Konigsberg, W. H. (1983) in "Bacteriophage T4", Eds: Mathews, C. K., Kutler, E. M., Mosig, G. and Berget, P. B. (*Am. Soc. Microbiol.*, Washington, D.C.), pp. 291–301; Adari, H. Y., Rose, K., Williams, K. R., Konigsberg, W. H., Lin, T. C., and Spicer, E. K. (1985), *Proc. Natl. Acad. Sci. USA* 82: 1901–1905), and regA gene has been overexpressed, Adari ibid. A map of these genes and the location of the gene 43 promoter and ribosome binding site are shown in FIG. 1. Cloning of gene 43 was started by transferring the $NH_2$-terminus of gene 43, from λ 761-4 (from Wilson, G. G. and Murray, N. E., New England Biolabs) (for vector NM 761, see Wilson, G. G., Tanyashin, V. I., and Murray, N. E. (1977) *Molec. Gen. Genet.* 156: 203-214), into puC9. Other phages can be used as well. Phage λ 761-4 contains a 5.62 kb T4 Hind III fragment from map unit 26.68 to 32.30 kb (see FIG. 1a upper) of the T4 genome. This Hind III fragment codes genes 45, 44, 62, regA and the $NH_2$-terminus of gene 43 L (missing 7 amino acids at COOH terminus, see below).

Figure 1A:
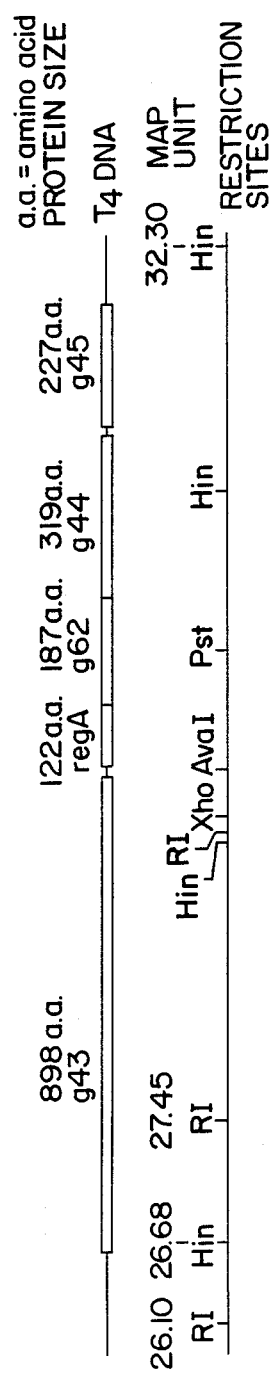
FIG. 1a illustrates the gene map of the T4 genome in the region of gene 43 (kb units refer to the distance from the γII A-γII B junction (Kutter, E. M. and Rueger, W. (1983) in *Bacteriophage T4*, eds. Matthews, C. K., Kutter, E. M., Mosig, G. and Berget P. B. (Am. Soc. Microbiol, Washington, D.C.), pp. 277–290); the direction of transcription of the five genes is from right to left)

A 3.99 kb PstI fragment (including the COOH-terminus of gene 62, regA, the NH$_2$-terminus of gene 43, and a portion of λ phage DNA) was transferred from 761-4 into pUC9, and a recombinant plasmid p43NR was isolated, as shown in FIG. 1b. Then a DNA fragment, including the COOH-terminus of gene 62, regA, and the promoter of gene 43, was deleted from p43NR by BHI and partial AvaI digestion, and a BHI linker was inserted into the deletion site to produce plasmid p43N (see FIG. 1b lower).

Figure 4:
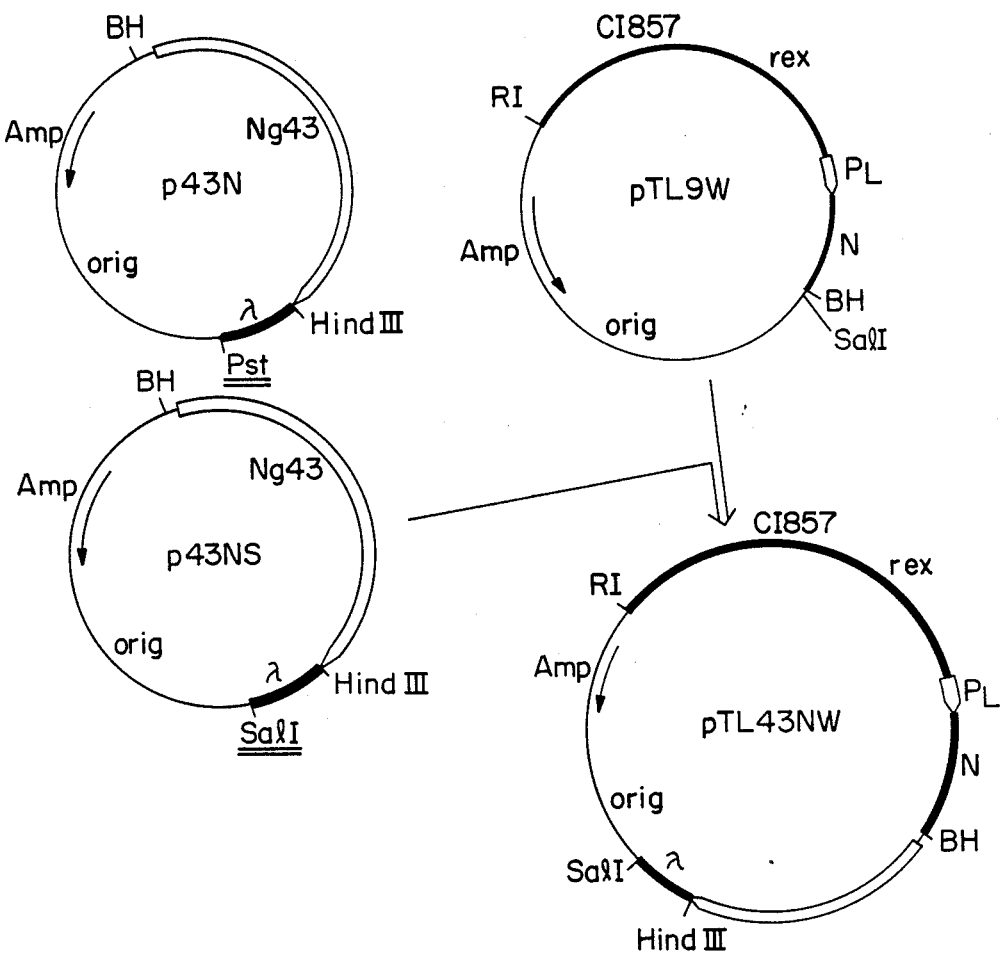
FIG. 4 illustrates recombinant procedures used to prepare plasmid pTL43NW.

More particularly with reference to FIG. 1(b), 761-4 was cut with pstI, and the pstI fragment containing gene 43 was ligated with pstI treated puc9 to yield p43NR. p43NR was first linearized with BHI, and then partially cut with AvaI to remove part of T4 DNA (including the COOH terminus of gene 62, regA gene and the promoter of gene 43 but not its ribosome binding site). The remaining part of p43NR was treated with Klenow's and ligated with BHI linker to yield p43N. p43N contains the ribosome binding site of gene 43, 99% of gene 43, and a fragment of λ phage DNA. In FIG. 1(b), PRM=promoter; RBS=ribosome binding site; A=AcaI; BH=BHI; H=Hind III and P=PstI.

Other sources providing the NH$_2$ terminus fragment of gene 43 can also be employed. It is, for example, possible using fully conventional methods to extract the NH$_2$-terminus fragment from the full genome of a T4 phage including any desirable mutants or variants of wild type. The particular plasmids discussed above and below were utilized because of the particular strategy taken in the experiments reported herein. Of course, when using different strategies, e.g., when utilizing different sets of restriction endonucleases, many readily available plasmids and corresponding cloning procedures can be employed. The latter will conventionally be modified in accordance with the particular strategy adopted. For instance, in the foregoing procedure, it is necessary to conduct a conventional partial digestion using AvaI which is effective to cleave the AvaI site shown in FIG. 1a but not a second AvaI site which exists in gene 43 and is not shown in the map. In other strategies, similar conventional means may be necessary.

Once having the NH2-terminus fragment, this must be joined to the remaining COOH-terminus fragment.

In the past, attempts have been made to clone the COOH-terminus of gene 43 via direct cloning of the Hind III-RI fragment (map:26.68 to 26.10 kb) from cytosine-containing T4 alc- GT7 into pUC8 or mp8. These failed. These prior art difficulties have been overcome by the following unique approach. This involves the discovery of the problem that the sequence beyond the end of the COOH-terminus causes the adverse properties discussed above, typically destabilization of a vector into which the final DNA sequence is inserted or adverse effects on any other aspect on the cloning process.

In order to obtain the missing COOH-terminus fragment, the full gene of a T4 bacteriophage not refractory to restriction endonucleases was sonicated—not fragmented by restriction endonucleases. Any such T4 bacteriophage can be used to provide the genome. In a preferred embodiment, the phage T4 alc-GT7 was utilized. Based on preliminary experiments reported in Experiment 1 below, it was determined that the NH$_2$-terminus containing fragment discussed above lacked only a few amino acids. Based on these results, using fully conventional considerations and fully conventional sonication equipment, sonication conditions were chosen to fragment the alc-GT7 DNA into pieces of approximately 300–600 bp, average. (See Experiment 2.) Using fully conventional procedures, these fragments were ligated into the smaI site of phage mp8 in order to conventionally create a T4/m 13 library. This library was then conventionally screened to select for individuals which were hybridized by a T4 RI-Hind III fragment probe (map:27.45 to 26.68 kb). One of the positively selected clones was designated m13/KR4C. A second clone was positive in the hybridization and can be successfully utilized in the procedures reported below.

DNA sequencing revealed that m13/KR4C, not only carries the sequence specified by the Hind III end of the probe, but also additional nucleotides. The additional nucleotides are long enough to encode 7 amino acids followed by inframe TGATAG double termination codons. The DNA sequence of the entire gene 43 and that of the region just outside its NH$_2$-terminus are shown in Table 1. In m13/KR4C, the COOH-terminus of gene 43 was cloned in a BHI to RI orientation within the mp8 cloning sites as shown in FIG. 1(c).

To construct a full length gene 43 clone, the routine steps shown in FIG. 1(c) were taken. First, a XhoI linker was inserted into the pUC18 NdeI site to yield pTL18X1. Then a XhoI linker was inserted into the R1 site of m13/KR4C. The COOH-terminus of gene 43, sandwiched by the BHI and XhoI site, was then transferred into pTL18X1 between the BHI and XhoI sites. p43C was obtained. Finally, the BHI-Hind III fragment (99% of gene 43 DNA) from p43N was transferred into the BHI-Hind III sites of p43c. The entire gene 43 was joined together and pTL43 was obtained.

The foregoing experiment can be effectively repeated, i.e., to provide a clonable gene 43 in view of the guidance of this application. For any given T4 genome library, sonification conditions can be conventionally varied to achieve the desired range of fragment size. Greater periods of sonification, of course, lead to smaller fragments, and vice versa. Although it is critical to this invention that the DNA sequence beyond the COOH-terminus not be so large that the destabilizing effects mentioned above are observed in the cloning process, the precise extent of this external sequence is otherwise not critical. Accordingly, under any reasonable sonification conditions using routine experimentation, a fragment encoding the necessry COOH-terminus but not encoding too many base pairs beyond the terminus will be obtained from any T4 genome library. The number of base pairs beyond the COOH-terminus which can be tolerated in accordance with this invention is approximately 50. The precise number is not critical since for any candidate fragment, by routine experimentation, it can be determined whether the undesired destabilization effects do in fact occur. Of course, in view of the guidance provided by the application, especially in view of the complete sequence of gene 43 reported herein, for any fragment of the NH$_2$-terminus, a corresponding fragment needed to complete the gene up to the COOH-terminus can always be prepared synthetically if desired and ligated using fully conventional methods.

With more particularity in reference to FIG. 1c, phage m13/KR4C (selected from a sonicated T4 fragment/mp8 Library) contains the COOH-terminus of gene 43, which is missing in p43N. The COOH-terminus in m13/KR4C is the portion of DNA starting from Hind III site toward the RI site. To join this portion of DNA with p43N, first, m13/KR4C was cut with RI, treated with Klenow's, ligated with xhoI linker, and then cut by xhoI and BHI. The BHI-xhoI fragment was then ligated with xhoI and BHI treated pTL18X1 (a pUC18 derivative, created by inserting a xhoI linker into the NdeI site) to yield p43c. Finally, the 99% of gene 43 was taken out from p43N by BHI and partial Hind III digestion and ligated into BHI-Hind III treated p43C to yield p43. p43 contains the whole length of gene 43, with its ribosome binding site and without its promoter. In FIG. 1(c), BH=BHI; H=Hind III; R=RI; x=xhoI; and RBS=ribosome binding site.

Once the intact gene is obtained without the troublesome portions outside its two termini, routine recombinant procedures can be utilized to express the gene. Since the latter lacks its own promoter, of course, the methodology must provide gene regulation means. Any of the many conventional methods for accomplishing this can be utilized. Moreover, when T4 DNA polymerase is toxic to the host, as it is to most applicable microorganisms, it will correspondingly be necessary to use a system wherein the host can grow absent expression of the gene. After sufficient growth, gene expression can be induced.

Accordingly, preferred methods for cloning the gene in accordance with this invention include its incorporation into a plasmid/host combination where it is regulated by an inducible promoter. In one preferred embodiment, the plasmid will incorporate the λ PL promoter and an appropriate inducing methodology, e.g., copresence of a temperature sensitive repressor gene such as the well known CI857. In another preferred embodiment, the plasmid used contains the inducible ptac promoter which can be induced by IPTG (isopropylthiogalactoside). The latter plasmid, of course, must be used in conjunction with a host which encodes the lac repressor. Many other promoter/inducer systems will be readily apparent to those of skill in the art. However, the two promoters mentioned above are preferred because they are very strong promoters thereby enabling high yields, and yet they also provide a high degree of regulation whereby tight control can be maintained to avoid toxicity to the host.

Figure 2:
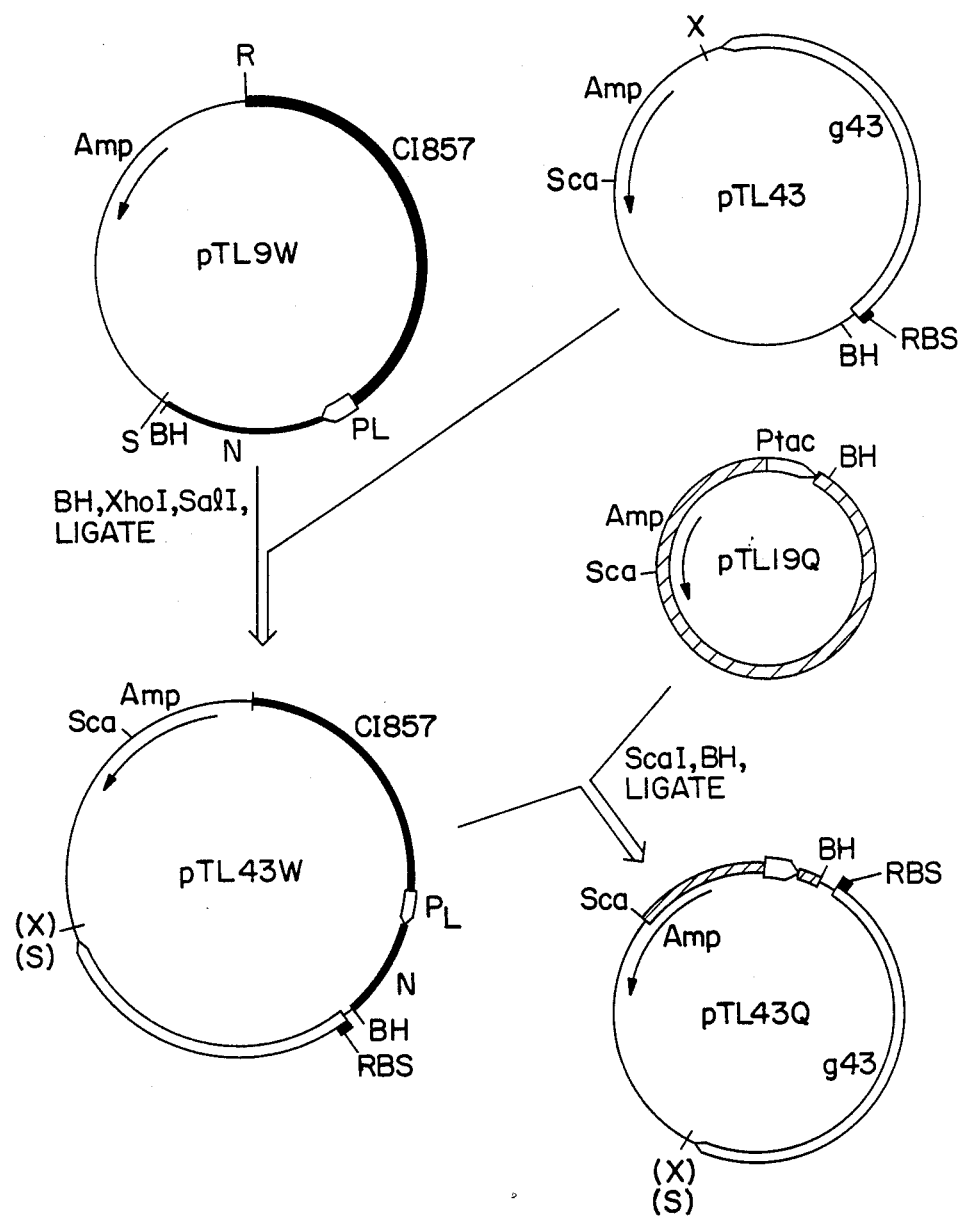
FIG. 2 illustrates recombinant procedures used to incorporate gene 43 into overexpression vectors.

To overexpress gene 43, its DNA from pTL43 was transferred into an overexpression vector pTL9W (FIG. 2). Construction of this vector is reported in Experiment 3. pTL9W carries the λ phage PL promoter and the CI857 temperature sensitive repressor gene, with BHI and SalI cloning sites located downstream of the PL promoter. Gene 43 DNA was excised out from pTL43 by BHI-xhoI digestion and ligated between the BHI and SalI sites of pTL9W. pTL43W was obtained. E. coli carrying pTL43W was induced to overexpress gene 43 protein by a temperature shift from the growth temperature of 30° C. to an induction temperature 40° C. Gene 43 protein was overproduced.

Gene 43 protein was also overproduced by using overexpression vector pTL19Q (FIG. 2). Construction of this vector is reported in Experiment 4. PTL19Q carries the IPTG inducible ptac promoter, with the multiple cloning site of pUC19 located downstream of the ptac promoter. To clone gene 43 under ptac control, the PL-CI region was removed from pTL43W by a ScaI-BHI cut and replaced by a scaI-BHI fragment (containing the ptac promoter) from pTL19Q. pTL43Q was obtained. When E. coli carrying pTL43Q was induced by adding IPTG to the culture, gene 43 was overproduced.

In a typical culture, E. coli carrying pTL43W was induced to overproduce gene 43 protein by a temperature shift. Cells were grown in Luria broth (Miller, J. H. (1972) Experiments in Molecular Genetics (Cold Spring Harbor Laboratory, Cold Spring Harbor, N.Y.) containing 50 μg of ampicillin per ml at 30° C. to $A_{590(nm)}=0.4 \sim 1.0$. The culture was then shifted to 40° C. for 2–6 hrs. E. coli carrying pTL43Q was induced to overproduce gene 43 protein by IPTG induction. Cells were grown in Luria broth containing 50 μg of ampicillin per ml at 37° C. to $A_{590}=0.4 \sim 1.0$. The culture was then supplied with 0.1M IPTG, purchased from Sigma Co. to a final concentration of 0.3 mM. Incubation continued for 2–6 hrs.

Induced cells were harvested by centrifugation. Most of the T4 DNA polymerase remained in the supernatant after cell lysis and low speed centrifugation. Overproduction was successful to the extent of over 10% (e.g., up to 30%) of total cell protein.

Of course, details of the culturing method can be conventionally varied. For the pTL43Q plasmid, as mentioned, the E. coli must have its own gene for expressing the lac repressor. If it is desired to utilize other bacteria, this can be accomplished in light of conventional considerations and procedures. For example, starting with pTL43W, the gene 43 sequence can be excised and incorporated into an appropriate vector. Similarly, vector systems other than those of this invention derived from pGW7 or ptac 12 plasmid can correspondingly be utilized. As is known, for the λ PL promoter, suitable growth conditions which do not induce the promoter include temperatures up to 33° C. Suitable induction temperatures are in the range of 39°–41° C. Gene 43 overexpressed at about 42° C. or a higher temperature forms an insoluble aggregation inside E. coli cells.

Routine isolation and purification procedures can be employed in accordance with this invention to prepare T4 DNA polymerase suitable for use in recombinant DNA technologies. Of course, it is possible conventionally from the isolated DNA sequence reported herein which codes for the DNA polymerase, to use it or portions thereof as probes in conjunction with gene banks of other T4 bacteriophages to identify and enable conventional isolation of corresponding genes from any such bank. Followed by conventional vector formation and host transformation, the corresponding DNA polymerases and mutants or variants can be produced The plasmids pTL43W and pTL43Q have been deposited with American Type Culture Collection in Rockville, Md., and bear accession numbers 40259 and 40256, respectively.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLE 1

Because of the overproduction of T4 DNA polymerase enabled by this invention, the conventional, tedious purification procedures can be avoided. Simpler methods such as that developed for the purification of overproduced Klenow fragment (Joyce, C. M. and Grindly, N. D. F., *Proc. Natl. Acad. Sci. USA* 80: 1830–1834 (1983) and rho protein from *E. coli* (Finger, L. R. F., and Richardson, J. P., *Biochemistry* 20: 1640–1645 (1981); Sharp, J. A., Galloway, J. L., and Platt, T. P., *J. Biol. Chem.*, 258: 3482–3486 (1983)) can be employed. As mentioned, under typical stable conditions, over 10% of the total protein produced by the *E. coli* will be T4 DNA polymerase. These yields are more than 100 times higher than the amount of polymerase produced by high producing T4 mutants and several hundred times higher than the amounts produced by normal T4 phage when used to infect *E. coli* cells.

Figure 3:
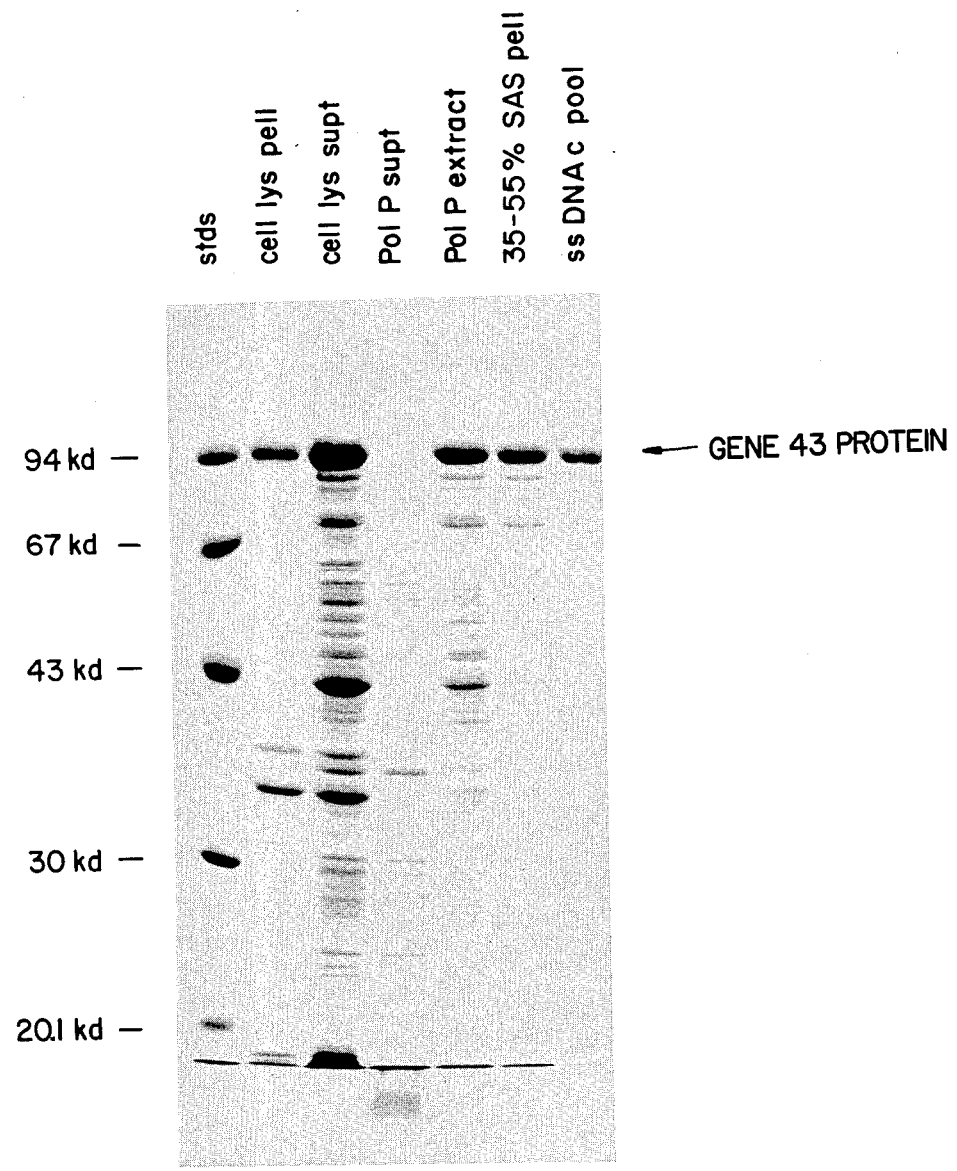
FIG. 3 provides a summary of gene 43 protein purification.

Overproducing cells which have undergone induction at 40° C. are first lysed by treatment with lysozyme, EDTA and deoxycholate. The viscosity of the lysate is then reduced by sonication. Protein expressed by gene 43 (43p) is precipitated from the cell lysate supernatant with polyethyleneimine (PEI), after determining the proper amount of PEI to use in a small scale pilot precipitation. After extracting 43p from PEI pellet, it is separated from residual PEI and concentrated by ammonium sulfate precipitation. 43p is further purified by passage over a single-stranded DNA cellulose column and is eluted with a step gradient. This simple procedure requires only three days to complete. This is a significant savings in the time over the conventional procedure which had required about 11 days to complete. The final product is greater than 98% pure and gave a single band on SDS PAGE (See FIG. 3). Using further conventional purification procedures, of course, higher purities can be obtained where necessary or desired.

EXAMPLE 2

Using fully conventional experimental techniques, the following characteristic properties of the T4 DNA polymerase prepared by the process of this invention have been measured:

A. Enzymatic and binding activities
 i. polymerase activity—comparison of 43op (overproduced) to 43P (purified from T4-infected cells) shows that 43op is equally active a polymerase as is the corresponding 43P.
 ii. exonuclease activity—comparisons as above show that 43op and 43P have the same level of exonuclease activity.
 iii. binding to DNA—43op binds to a single-stranded DNA cellulose column and is eluted, within experimental error, by the same concentration of salt as 43P—of course, if it could not bind DNA, it would have neither of the enzymatic activities above.
 iv. binding to 32P (T4 gene 32 protein)—43op binds to a column of immobilized 32P and is eluted within the salt range expected for 43P.

B. Protein chemical characterization
 i. amino acid composition of 43op is similar to what would be expected of 43P from the sequence of gene 43.
 ii. amino-terminal 15 residues are correct, as inferred from the sequence of gene 43 and from the empirically determined amino terminal sequence of 43P.
 iii. carboxy-terminal analysis indicates the presence of the residues expected from the sequence of gene 43.
 iv. comparative tryptic peptide mapping of 43op and 43P shows no significant differences.

EXPERIMENT 1

(Overexpression of p43N; See FIG. 4)

Figure 5:
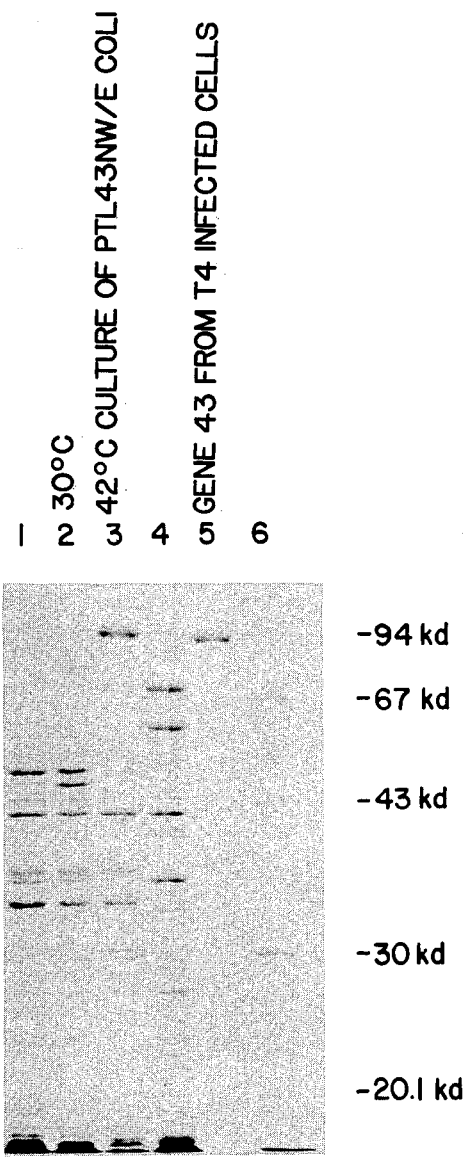
FIG. 5 shows SDS polyacrylamide gel analysis showing induction of insoluble 43P-lambda. Lane 1, total cell lysate of 71-18, the host cell. Lane 2, total cell lysate of 71-18 harboring pTL43NW, grown under noninducing conditions, at 30 degrees. Lanes 3 and 4, cell lysate pellet and supernatant, respectively, of 71-18 harboring PTL43NW grown under inducing conditions, at 42 degrees. Lane 5, 43P purified from T4-infected cells. Lane 6, molecular weight standards.

To overexpress the $NH_2$-terminus of partial gene 43 cloned in p43N, the following steps were taken. First, a SalI linker (GGTCGACC) was inserted into the pstI site of p43N, to create a SalI site at that point. Plasmid p43NS was obtained. The DNA fragment including the $NH_2$-terminus of gene 43 and a segment of λ DNA (carried over from λ phage during the transferring of gene 43 DNA from λ 761-4 to puc 9) was obtained from p43NS by BHI-salI digestion, and was ligated into the BHI-salI sites of pTL9W. (See Experiment 3 for the construction of pTL9W.) The product, pTL43NW, contains the PL promoter, the CI857 temperature sensitive repressor, the $NH_2$-terminus of gene 43, and a segment of λ DNA. When *E. coli* carrying pTL43NW was grown at 30° C. to $A_{590}=0.4$, and then shifted to 42° C. for 4 hrs, a gene 43.λ fusion protein was overexpressed. When the cell extract of the 42° C. incubated culture was analyzed on a SDS-polyacrylamide gel (lane 3 of FIG. 5), the gene 43.λ fusion protein was observed.

The fusion of gene 43 and λ DNA segment occurs at the Hind III site. Since the nucleotide sequence of the λ DNA segment is

| AAGCTT | TG | TGT | GCC | ACC | CAC | TAC | GAC | CTG | CAT | AAC | CAG | TAA |
|--------|----|-----|-----|-----|-----|-----|-----|-----|-----|-----|-----|------|
| HindIII | 1 | 2 | 3 | 4 | 5 | 6 | 7 | 8 | 9 | 10 | 11 | stop, | etc. (nucleotide no. 27476 to 27456; Sanger, F., Goulson, A. R., Hong, G. F., Hill, D. F., and Petersen, G. B. (1982) *J. Mol. Bio.* 162: 729–773), the gene 43.λ fusion protein must have carried 11 amino acids from coding. The molecule weight of the gene 43.λ protein is about the same as that of the natural gene 43 protein (lane 5 of FIG. 5), judged by their mobilities on SDS-polyacrylamide gel. Thus, it was concluded that the COOH-terminus of gene 43, missing in p43N (and pTL43NW), must be coding for only a very few additional amino acids.

The overproduced gene 43.λ fusion protein could not be purified in large quantity. When gene 43.λ protein was overexpressed at 42° C., it formed insoluble protein aggregates. When the induction temperature was lowered to 40° C., gene 43.λ protein did not aggregate, but it was proteolytically digested by *E. coli* proteases.

EXPERIMENT 2

(Sonication of T4 bacteriophage genome of T4 alc-GT7)

About 20 μg of DNA in 10 mm Tris.HCl, 1 mM EDTA(pH8) was sonicated. The sonicator was "Heat Systems", by Ultrasonic Incorporated. A microprobe was used at power setting 4. Six bursts of sonication were applied. Each burst lasted 20 seconds, with a 30 second break between bursts. The DNA tube was kept cool by surrounding it with ice-water during sonication. After the sonication, the DNA was treated with conventional phenol/chloroform extraction, and then precipitated with ethanol. The sonicated DNA fragment was redissolved in buffer and blunt ended by incubation with Klenow's polymerase before cloning.

EXPERIMENT 3

Figure 6:
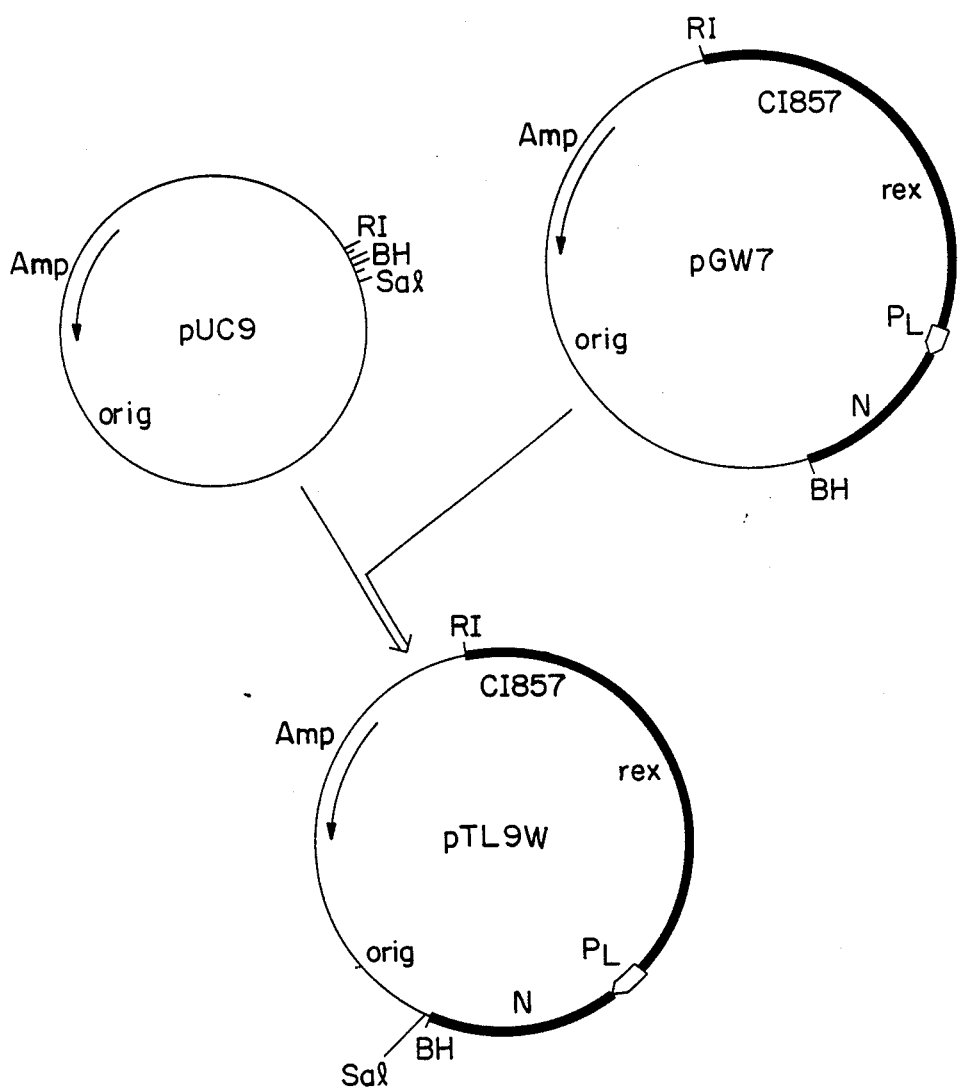
FIG. 6 shows recombinant procedures used to prepare plasmid pTL9W.

(Construction of pTL9W; see FIG. 6)

Plasmid pTL19W was constructed by transferring a fragment of λ phage DNA from PGW7 (G. G. Wilson) into puc9. The λ DNA fragment was cleaved out from pGW7 by RI.BHI treatment, and was ligated into the RI/BHI sites of puc 9.

EXPERIMENT 4

Figure 7:
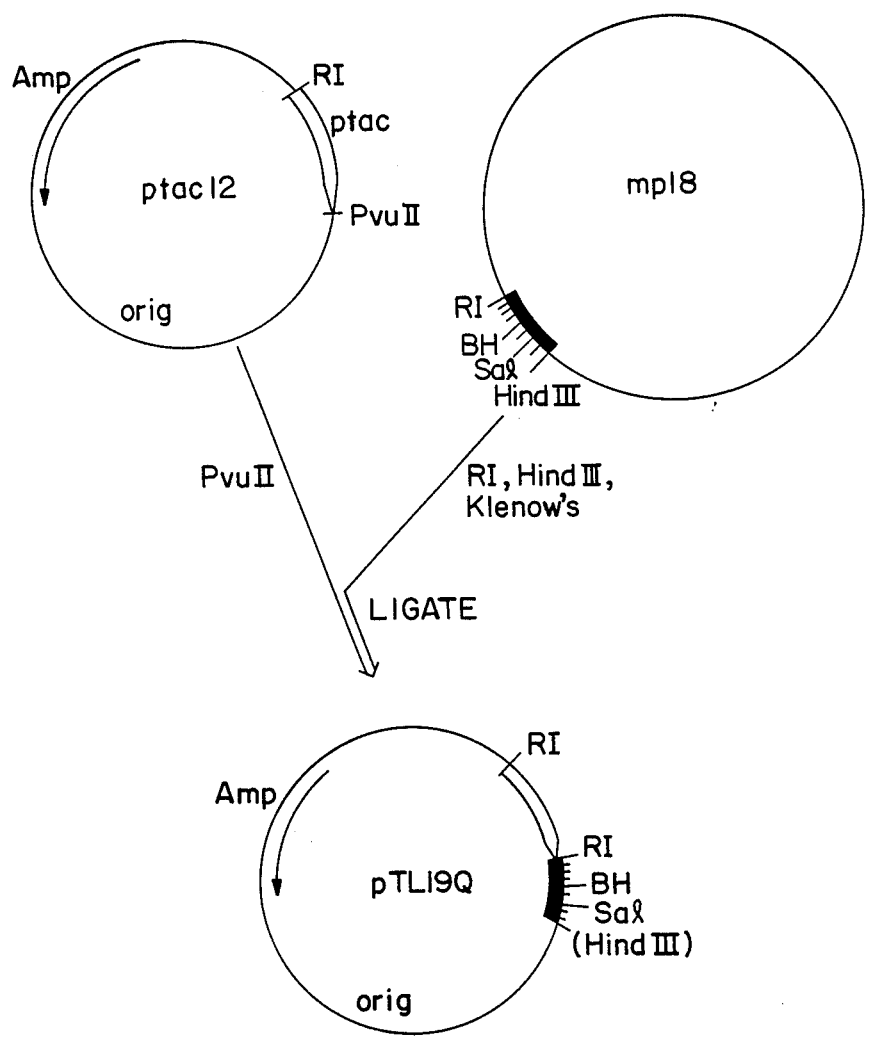
FIG. 7 illustrates recombinant procedures used to prepare plasmid pTL19Q.

(Construction of pTL19Q; see FIG. 7)

Plasmid pTL19Q was constructed by inserting the multiple restriction sites region of mp18, into the pvuII site of ptac 12 (Amann, E. Brosius, J. and Ptashne, M. Gene 25 (1983) 167–178). The DNA fragment containing the multiple restriction sites was cleaved out from mp18 by RI and HindIII cuts, blund ended with Klenow's fragment, and then ligated into the pvaII site of ptac 12.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A recombinant cloning vector comprising a DNA sequence encoding a polypeptide having bacteriophage T4 DNA polymerase activity.

2. A vector of claim 1, which is a plasmid.

3. A plasmid of claim 2, which is a replicable expression vector capable, in a transformant microorganism or cell culture, of expressing said DNA sequence.

4. A plasmid of claim 3, comprising an inducible promoter effective to control expression of said DNA sequence, whereby when said plasmid is used to transform a suitable host, said promoter can be turned off under conditions in which said host will grow and can then be turned on under corresponding inducing conditions.

5. A plasmid of claim 4, wherein said promoter is inducible by a temperature change or a repressor/inducer combination.

6. A plasmid of claim 5, wherein said inducible promoter comprises a combination in said plasmid of the phage PL promoter and temperature sensitive repressor gene CI857, or is IPTG inducible ptac promoter.

7. pTL43W, a plasmid of claim 5.

8. pTL43Q, a plasmid of claim 5.

9. An isolated DNA molecule encoding a polypeptide having bacteriophage T4 DNA polymerase activity.

10. A DNA sequence of claim 9, ATGAAAGAA TTTTATATCT CTATTGAAAC AGTCGGAAAT AACATTGTTG AACGTTATAT TGATGAAAAT GGAAAGGAAC GTACCCGTGA AGTAGAATAT CTTCCAACTA TGTTTAGGCA TTGTAAGGAA GAGTCAAAAT ACAAAGACAT CTATGGTAAA AACTGCGCTC CTCAAAAATT TCCATCAATG AAAGATGCTC GAGATTGGAT GAAGCGAATG GAAGACATCG GTCTCGAAGC TCTCGGTATG AACGATTTTA AACTCGCTTA TATAAGTGAT ACATATGGTT CAGAAATTGT TTATGACCGA AAATTTGTTC GTGTAGCTAA CTGTGACATT GAGGTTACTG GTGATAAATT TCCTGACCCA ATGAAAGCAG AATATGAAAT TGATGCTATC ACTCATTACG ATTCAATTGA CGATCGTTTT TATGTTTTCG ACCTTTTGAA TTCAATGTAC GGTTCAGTAT CAAAATGGGA TGCAAAGTTA GCTGCTAAGC TTGACTGTGA AGGTGGTGAT GACGTTCCTC AAGAAATTCT TGACCGAGTA ATTTATATGC CATTCGATAA TGAGCGTGAT ATGCTATGG AATATATCAA TCTTTGGGAA CAGAAACGAC CTGCTATTTT TACTGGTTGG AATATTGAGG GGTTTGACGT TCCGTATATC ATGAATCGTG TTAAAATGAT TCTGGGTGAA CGTAGTATGA AACGTTTCTC TCCAATCGGT CGGGTAAAAT CTAAACTAAT TCAAAATATG TACGGTAGCA AAGAAATTTA TTCTATTGAT GGCGTATCTA TTCTTGATTA TTTAGATTTG TACAAGAAAT TCGCTTTTAC TAATTTGCCG TCATTCTCTT TGGAATCAGT TGCTCAACAT GAAACCAAAA AAGGTAAATT ACCATACGAC GGTCCTATTA ATAAACTTCG TGAGACTAAT CATCAACGAT ACATTAGTTA TAACATCATT GACGTAGAAT CAGTTCAAGC AATCGATAAA ATTCGTGGGT TTATCGATCT ACTTTTAAGT ATGTCTTATT ACGCTAAAAT GCCTTTTTCT GGTGTAATGA GTCCTATTA AACTTGGGAT GCTATTATTT TTAACTCATT GAAAGGTGAA CATAAGGTTA TTCCTCAACA AGGTTCGCAC GTTAAACAGA GTTTTCCGGG TGCATTTGTG TTTGAACCTA AACCAATTGC ACGTCGATAC ATTATGAGTT TTGACTTGAC GTCTCTGTAT CCGAGCATTA TTCGCCAGGT TAACATTAGT CCTGAAACTA TTCGTGGTCA GTTTAAAGTT CATCCAATTC ATGAATATAT CGCAGGAACA GCTCCTAAAC CGAGTGATGA ATATTCTTGT TCTCCGAATG GATGGATGTA TGATAAACAT CAAGAAGGTA TCATTCCAAA GGAAATCGCT AAAGTATTTT TCCAGCGTAA AGACTGGAAA AAGAAAATGT TCGCTGAAGA AATGAATGCC GAAGCTATTA AAAAGATTAT TATGAAAGGC GCAGGGTCTT GTTCAACTAA ACCAGAAGTT GAACGATATG TTAAGTTCAG TGATGATTTC TTAAATGAAC TATCGAATTA CACCGAATCT GTTCTCAATA GTCTGATTGA AGAATGTGAA AAAGCAGCTA CACTTGCTAA TACAAATCAG CTGAACCGTA AAATTCTCAT TAACAGTCTT TATGGTGCTC TTGGTAATAT TCATTTCCGT TACTATGATT TGCGAAATGC TACTGCTATC ACAATTTTCG GCCAAGTCGG TATTCAGTGG ATTGCTGCTA AAATTAATGA ATATCTGAAT AAAGTATGCG GAACTAATGA TGAAGATTTC ATTGCAGCAG GTGATACTGA TTCGGTATAT GTTTGCGTAG ATAAAGTTAT TGAAAAAGTT GGTCTTGACC GATTCAAAGA GCAGAACGAT TTGGTTGAAT TCATGAATCA GTTCGGTAAG AAAAAGATGG AACCTATGAT TGATGTTGCA TATCGTGAGT TATGTGATTA TATGAATAAC CGCGAGCATC TGATGCATAT GGACCGTGAA GCTATTTCTT GCCCTCCGCT TGGTTCAAAG GGCGTTGGTG GATTTT- GGAA AGCGAAAAAG CGTTATGCTC TGAACGTTTA TGATATGGAA GATAAGCGAT TTGCTGAACC GCATCTAAAA ATCATGGGTA TGGAAACTCA GCAGAGTTCA ACACCAAAAG CAGTGCAAGA AGCTCTCGAA GAAAGTATTC GTCGTATTCT TCAGGAAGGT GAAGAGTCTG TCCAAGAATA CTACAAGAAC TTCGAGAAAG AATATCGTCA ACTGACTATA AGTATGCTGA GTAAAAACTG CGAACGATAT AGCGAATATG ATGATAAAGG TTGGCCAGGA TTTAAATGCC CGTTCCATAT TCGTGGTGTG CTAACTTATC GTCGAGCTGT TAGCGGTTTA GGTGTAGCTC CAATTTTGGA TGGAAATAAA GTAATGGTTC TTCCATTACG TGAAGGAAAT CCATTTGGTG ACAAGTGCAT TGCTTGGCCA TCGGGTACAG AACTTCCAAA AGAAATTCGT TCTGATGTGC TATCTTGGAT TGACCACTCA ACTTTGTTCC AAAAATCGTT TGTTAAACCG CTGGCGGGTA TGTGTGAATC GGCTGGCATG GACTATGAAG AAAAAGCTTC GTTAGACTTC CTGTTTGGCT GATAG.

11. A DNA sequence which is a mutation of that of claim 10 and which codes for a polypeptide having bacteriophage T4 DNA polymerase activity.

12. A microorganism or cell culture transformed with the vector of claim 4.

13. A microorganism of claim 12 obtained by transforming an *E. coli* strain.

14. A method for producing a polypeptide having bacteriophage T4 DNA polymerase activity comprising expressing the T4 DNA polymerase-encoding DNA sequence of the vector of claim 1 in a recombinant host.

15. A method of claim 14, wherein said expression is controlled by an inducible promoter.

16. A method of claim 15, comprising growing said host under growth conditions whereunder said promoter is repressed and thereafter inducing said promoter to express said DNA sequences.

17. A method of claim 16, wherein the promoter is inducible by a temperature change or a repressor/inducer combination.

18. A method of claim 17, wherein the promoter comprises, in a plasmid containing said DNA sequence, a combination of the λ phage PL promoter and the temperature sensitive repressor gene CI857, or said promoter is IPTG inducible ptac promoter where said host comprises a DNA sequence encoding the lac repressor.

19. A method of claim 18, wherein said vector is plasmid pTL43W.

20. A method of claim 18, wherein said vector is plasmid pTL43Q.

21. A method of producing a polypeptide having T4 DNA polymerase activity comprising:
transforming a host cell culture with a plasmid of claim 4 to obtain a recombinant host cell,
culturing said recombinant host cell under conditions permitting expression of the T4 DNA polymerase encoding sequence of said plasmid to produce T4 DNA polymerase, and.
recovering said polypeptide in substantially pure form.

22. An isolated DNA sequence which hybridizes with a DNA sequence of claim 10, and encoding a polypeptide having bacteriophage T4 DNA polymerase activity.

* * * * *

UNITED STATES PATENT AND TRADEMARK OFFICE
CERTIFICATE OF CORRECTION

PATENT NO. : 4,935,361
DATED : June 19, 1990
INVENTOR(S) : Tsung-Chung Lin et al It is certified that error appears in the above-identified patent and that said Letters Patent is hereby corrected as shown below:

Column 12, Claim 10, Line 29:

Reads: "ATTCGTGGGT TTATCGATCT ACTTTTAAGT"

Should Read: --ATTCGTGGGT TTATCGATCT AGTTTTAAGT--

Column 12, Claim 10, Line 56:

Reads: "TATTCAGTGG ATTGCTGCTA AAATTAATGA"

Should Read: --TATTCAGTGG ATTGCTCGTA AAATTAATGA--

Column 13, Claim 10, Line 20:

Reads: "TGTTAAACCG    CTGGCGGGTA"

Should Read: --TGTTAAACCG    CTTGCGGGTA--

Signed and Sealed this

Eighth Day of October, 1991

*Attest:*

HARRY F. MANBECK, JR.

*Attesting Officer*    *Commissioner of Patents and Trademarks*